United States Patent
Lee (10) Patent No.: US 7,955,337 B2
(45) Date of Patent: Jun. 7, 2011

(54) FACIAL BONE CONTOURING DEVICE USING HOLLOWED RASP PROVIDED WITH NON-PLUGGING HOLES FORMED THROUGH CUTTING PLANE

(76) Inventor: Hee-Young Lee, Kunsan (KR)

( * ) Notice: Subject to any disclaimer, the term of this patent is extended or adjusted under 35 U.S.C. 154(b) by 668 days.

(21) Appl. No.: 10/519,442

(22) PCT Filed: Jun. 25, 2003

(86) PCT No.: PCT/KR03/01250
§ 371 (c)(1),
(2), (4) Date: Dec. 20, 2005

(87) PCT Pub. No.: WO2004/002331
PCT Pub. Date: Jan. 8, 2004

(65) Prior Publication Data
US 2006/0129159 A1    Jun. 15, 2006

(30) Foreign Application Priority Data
Jun. 29, 2002    (KR) .................. 10-2002-0037408

(51) Int. Cl.
*A61B 17/32*    (2006.01)
(52) U.S. Cl. ........................ 606/85; 606/86 R
(58) Field of Classification Search .......... 606/170–171, 606/79–85, 167–169, 172–183, 86 R; 623/17.17–17.19
See application file for complete search history.

(56) References Cited

U.S. PATENT DOCUMENTS

| | | | |
|---|---|---|---|
| 4,428,748 A * | 1/1984 | Peyman et al. | 604/22 |
| 4,625,725 A * | 12/1986 | Davison et al. | 606/85 |
| 4,766,701 A | 8/1988 | Rosetenberg | |
| 4,832,683 A * | 5/1989 | Idemoto et al. | 604/22 |
| 5,269,785 A * | 12/1993 | Bonutti | 606/80 |
| 5,269,798 A | 12/1993 | Winkler | |
| 5,286,253 A | 2/1994 | Fucci | |
| 5,364,395 A | 11/1994 | West, Jr. | |
| 5,387,215 A * | 2/1995 | Fisher | 606/79 |
| 5,403,276 A | 4/1995 | Schechter et al. | |
| 5,415,170 A * | 5/1995 | Hammerslag et al. | 600/434 |
| 5,419,774 A * | 5/1995 | Willard et al. | 604/22 |
| 5,456,689 A * | 10/1995 | Kresch et al. | 606/180 |
| 5,540,693 A * | 7/1996 | Fisher | 606/79 |
| 5,643,304 A * | 7/1997 | Schechter et al. | 606/171 |
| 5,685,840 A | 11/1997 | Schechter et al. | |
| 5,782,848 A * | 7/1998 | Lennox | 606/159 |
| 5,792,167 A | 8/1998 | Kabik | |
| 5,810,809 A * | 9/1998 | Rydell | 606/49 |
| 5,893,858 A * | 4/1999 | Spitz | 606/170 |

(Continued)

*Primary Examiner* — Thomas C Barrett
*Assistant Examiner* — Larry E Waggle, Jr.
(74) *Attorney, Agent, or Firm* — Ladas & Parry LLP (57) ABSTRACT

Disclosed is a facial bone contouring device for use in facial bone contouring surgery and bone tumor and/or osteophyte removal. The facial bone contouring device comprises: a rasp (10), having a double tube structure, including a rod (11), and a cutter (13) provided with plural grooves (13*c*) for exhausting cut bone fragments, a saline solution feeding passage (15) and a bone fragment exhausting passage (14); a powered surgical handpiece (40) connected to the rasp (10) for providing linear reciprocating motion to the rasp (10); a saline solution feeding unit (30) for feeding saline solution to the saline solution feeding passage; and a suction unit (20) for sucking and exhausting the cut bone fragments, wherein bone cutting is performed under the condition that the saline solution is fed into the rasp, and the cut bone fragments are exhausted together with the saline solution so that the bone cutting is continuously performed.

6 Claims, 7 Drawing Sheets

U.S. PATENT DOCUMENTS

| | | | | |
|---|---|---|---|---|
| 5,913,859 A | * | 6/1999 | Shapira | 606/80 |
| 6,007,556 A | * | 12/1999 | Kablik et al. | 606/180 |
| 6,048,345 A | * | 4/2000 | Berke et al. | 606/85 |
| 6,102,926 A | * | 8/2000 | Tartaglia et al. | 606/170 |
| 6,156,049 A | * | 12/2000 | Lovato et al. | 606/170 |
| 6,159,209 A | * | 12/2000 | Hakky | 606/45 |
| 6,332,886 B1 | | 12/2001 | Green et al. | |
| 6,368,324 B1 | | 4/2002 | Dinger et al. | |
| 6,511,493 B1 | * | 1/2003 | Moutafis et al. | 606/167 |
| 6,517,560 B1 | * | 2/2003 | Toth et al. | 606/171 |
| 6,827,725 B2 | * | 12/2004 | Batchelor et al. | 606/170 |
| 2001/0000531 A1 | * | 4/2001 | Casscells et al. | 606/49 |
| 2001/0037114 A1 | * | 11/2001 | Dinger et al. | 606/85 |
| 2001/0047183 A1 | * | 11/2001 | Privitera et al. | 606/170 |

* cited by examiner

FACIAL BONE CONTOURING DEVICE USING HOLLOWED RASP PROVIDED WITH NON-PLUGGING HOLES FORMED THROUGH CUTTING PLANE

TECHNICAL FIELD

The present invention relates to a contouring device for use in facial bone contouring surgery such as mandibular angle reduction and maloplasty, and removal of bone tumor and/or osteophyte, and more particularly to a facial bone contouring continuous cutting device using a small-sized rasp, which is able to be inserted beneath the skin and cut bone, provided with bone fragment exhausting means and saline solution feeding means and attached to a handpiece with linear reciprocating means, which can be inserted beneath the skin through a minimum-sized incision and delivered to a bone cutting site to carry out facial bone contouring surgery.

BACKGROUND ART

Generally, a conventional method used in facial bone contouring surgery employs a bone-cutting saw for cutting bone at a desired site. Since a large quantity of bone is cut using such a saw at once, the accuracy in bone cutting is difficult to achieve.

In order to accurately set a cutting angle, easily eliminate cut bone fragments from the bone and easily deliver the rasp to the desired cutting site, the above conventional method essentially requires that a visual field of the surgeon be secured, thus a large-sized incision for securing the visual field being needed. Accordingly, the conventional method has several problems such as severe swelling and excessive bleeding of the cutting site, delayed healing, cutting of vessels, nerve damage, etc.

Further, the saw for cutting bone may cause severe injuries to peripheral soft tissues around the incision during the movement.

Thus, there is required a more stable bone cutting method using a rasp. However, since there is not yet developed any device to meet this requirement, it is difficult to stably perform surgery using the rasp.

Compared with other surgeries, the facial bone contouring surgery must continuously grind down a large amount of bone in a short period of time, exhaust muscles and periosteum together with the ground bone fragments, and carry out the whole process thereof for a short time so as to minimize the bleeding and swelling of the incision. Further, since the facial bone contouring surgery requires a step of generally reducing the thickness of bone, an effective cutting plane contacting the bone must be a large area. Since bone fragments are accumulated, aggregated and compressed between blades of the conventional rasp during the operation, continuous cutting using the rasp is impossible. Thus, since blades of electric-powered or pneumatic rasps must be cleaned off every several seconds, it is impossible to grind a large amount of bone using these rasps in the facial bone contouring surgery. Further, the stacking of the bone fragments on the blades is made more severe by heat generated from the cutting plane of the electric-powered or pneumatic rasps. On the other hand, hand-powered rasps do not generate heat but have a low operational speed, thus being impractical to use.

The conventional electric-powered or pneumatic devices cannot be inserted under the skin via a small incision so as to continuously grind a large amount of bone. These conventional devices have limitedly been used to remove a small amount of bone. However, these devices have a structure which cannot be used in facial bone contouring surgery. Further, in order to use a device in the facial bone contouring surgery, the device must have a constitution such that muscle fragments and periosteum with comparatively large sizes together with the ground bone fragments are exhausted from the body to the outside. Simultaneously, in order to allow the device to be inserted beneath the skin via a small incision, the device must have a cutting plane with large length relative to the outer diameter of the device. However, the conventional devices do not meet these requirements, thus not being used in facial bone contouring surgery.

A bone cutting rasp used in facial bone contouring surgery is used at a position and angle differing from those of the conventional bone cutting device. That is, a small-sized osteophyte or cartilage can be removed by a rasp with a small interface with the osteophyte or cartilage, while a broad, flat and solid surface of a facial bone is ground to have a desired shape by a rasp with a broad interface with the surface of the facial bone. The cutting plane of the rasp required to grind the facial bone (such as mandibular angle and zygomatic bone contouring) is maximally 40 mm. In order to uniformly grind the facial bone, the rasp must have a length of at least 30 mm.

U.S. Pat. No. 6,368,324 discloses a surgical handpiece adaptor assembly comprising an adaptor with a mechanism for converting rotary motion of a powered surgical handpiece into reciprocating motion, and a cutting member, such as a rasp, provided with a tissue cutting surface and a suction passage with an inlet opening along the tissue cutting surface. The cutting member coupled with a distal end of a front drive shaft of the adaptor is inserted beneath the skin at an operative site for cutting and removing anatomical debris such as the nasal bone from the operative site at which the rasp is used.

The cutting member of this patent is delivered to the operative site via a minimum incision, cuts a desired bone in the operative site, and exhausts the cut fragments of the bone via the inlet, thus solving the above-described problems of the conventional bone-cutting saws.

However, this assembly cannot supply a saline solution to the cutting surface, thus not eliminating heat generated on the cutting surface when a large quantity of bone such as zygomatic bone, maxilla or mandible is continuously removed. Further, the inlet has a structure such that the continuous cutting of bone cannot be performed and bone debris aggregated and compressed between blades of the rasp cannot be exhausted to the outside, thus requiring frequent cleaning. Accordingly, this assembly can be used in surgical facial procedures such as rhinoplasty and supraorbital procedures, but cannot be effectively used in the skin overlying the area of the supraorbital bone that is to be reshaped or contoured.

That is, in the facial bone contouring surgery such as angle ostectomy or maloplasty, a large quantity of bone must be cut or ground off. Here, heat is generated due to friction between the rasp and the bone, thus causing damages such as burning of soft tissues or deformation of tissues. Further, the cut fragments of bone are aggregated during cutting and accumulated between blades of the rasp, thus not being exhausted to the outside and remarkably reducing the cutting efficiency of the assembly.

The bone cutting is also performed so as to collect bone fragments for bone tissue culture. Since the collected bone fragments are damaged by the heat generated due to friction between the rasp and the bone, it is difficult to use the damaged bone fragments in bone tissue culture. Further, during the driving of the cutting member, the cutting member irritates and damages peripheral soft tissues around the operative site.

Further, the assembly does not have a double tube structure, thus not protecting peripheral regions around the operative site during the insertion and operation of the rasp, and causing inconvenience to a surgeon in case that the rasp is inserted into the operative site via a small and deep incision. Since the friction generated between the cutting plane of the rasp operated at a high speed and the bone damages peripheral tissues, this assembly is not suitable for use in facial bone contouring surgery.

U.S. Pat. No. 5,540,693 discloses cutting means provided with a motor-driven cutter and a double conduit. However, since heat generated on this cutting means cannot be eliminated and bone crash is accumulated between blades of the cutter, the cutting means is not suitable for use in removal of a large quantity of bone or for facial bone contouring surgery. A shaft of the cutting means is used as a suction tube. Accordingly, the cutting means of this patent provides a broad passage via even a small incision, and has a double tube structure provided with a protection tube, thus protecting peripheral tissues around an operative site. However, an inlet does not pass through the cutting plane, thus generating many bone fragments and causing a difficulty in sucking large-sized tissue fragments.

U.S. Pat. Nos. 5,643,304 and 5,403,276 disclose motor-driven surgical rasps for use in cartilage and/or bone removal, each of which comprises a protective double cannula structure for feeding saline solution and sucking removed tissues via slits formed between blades of the rasp. This rasp prevents the aggregation of bone fragments and the damage of peripheral tissues due to frictional heat, but has several disadvantages. That is, the slits between the blades of the rasp are easily clogged with the cut bone fragments. Further, since the shaft of a cutter serves as a saline solution feeding pipe and an external pipe serves as a suction pipe, the external pipe must have an enlarged diameter so as to suck large-sized bone fragments.

Moreover, in this structure, the bone fragments obtained by grinding move toward a cutting plane along the inner wall of the rasp. Thus, this structure must have through-holes formed between the blades of the rasp so as to prevent the clogging of the bone fragments. Although the saline solution is sprayed via the through-holes, since the spraying pressure of the saline solution is smaller than the suction pressure of the bone fragments, the through-holes are easily clogged with the bone fragments. Therefore, in case that the through-holes of a part of the plural blades of the rasp are clogged with the bone fragments and do not spray saline solution, the number of usable blades of the rasp is reduced. Accordingly, this structure is usefully employed in a small cutter for removing a small quantity of bone, which includes only two or three blades and saline solution feeding slits, but is not employed in a large-sized long cutter for simultaneously removing a large quantity of bone, periosteum and muscles at a high speed, such as facial bone contouring surgery, which includes a plurality of blades.

In order to perform continuous cutting, comparatively large-sized holes must be formed through the cutting planes between the blades so that the suction pipe is formed according to the moving direction of the bone fragments and the direction of suction pressure. However, the above structure does not meet this requirement. Further, with the above structure, it is impossible to form the maximum cutting plane via the minimum outer diameter of the cutter. For this reason, the rasp having this structure is not used in facial bone contouring surgery.

This rasp is used in endoscopic operations such as operations on geniculate cartilage or spine. That is, the rasp having this structure is used to remove only a small quantity of tissues, which contact the exposed tip of the blade or are sucked by the external pipe, and a small-sized osteophyte. Accordingly, with the rasp, it is impossible to actively cut a broad, flat and solid plane of bone such as zygoma, maxilla or mandible.

U.S. Pat. No. 4,766,701 discloses a hand-powered vacuum rasp comprising a plurality of downward-facing openings formed through an abrading work surface. This hand-powered rasp sucks only air via the openings, but does not feed saline solution for removing generated heat and remove bone fragments at a high speed. Further, the rasp does not have a double cannula structure, and the size of the openings is not sufficient to suck the cut bone fragments together with air. Moreover, it is difficult to manufacture a cutter of the rasp being suitable for use in facial bone contouring surgery. The hand-powered vacuum rasp has a suction structure in a shaft of the cutter and suction openings formed through the cutting plane. However, the hand-powered vacuum rasp having this suction structure cannot be used in facial bone contouring surgery.

In addition, U.S. Pat. Nos. 5,269,798, 5,286,253, and 5,364,395 disclose various instruments for use in cartilage and/or bone removal, in which saline solution feeding and tissue cutting are simultaneously performed. However, these instruments perform the tissue cutting using a rotary blade, thus causing exposed portions of nerves and vessels in facial bone contouring surgery to be dangerously rolled into the blade. Further, these instruments remove only portions sucked into protrusions or an external pipe, thus not being used in reduction of a broad area such as facial bone contouring surgery.

DISCLOSURE OF THE INVENTION

Therefore, the present invention has been made in view of the above problems of the conventional surgical cutting instruments, and it is an object of the present invention to provide a facial bone contouring device using a rasp, which can be inserted beneath the skin via a small-sized incision and continuously cut bone at a cutting site into very small fragments, thus easily controlling the cutting amount of bone and drastically reducing the risk of medical accidents.

It is another object of the present invention to provide a facial bone contouring device using a rasp, which serves as means for collecting bone debris by bone grinding rather than bone cutting, used in facial bone contouring or face lifts.

It is yet another object of the present invention to provide a device for continuously and stably exhausting a large quantity of bone, periosteum and muscles at a high speed, in surgery in which a large quantity of bone, periosteum and muscles must be removed in a short period of time such as facial bone contouring surgery.

In accordance with the present invention, the above and other objects can be accomplished by the provision of a facial bone contouring device comprising: a rasp including a saline solution feeding passage and a bone fragment exhausting passage; a powered surgical handpiece including linear reciprocating means connected to the rasp for providing linear reciprocating motion to the rasp; a saline solution feeding unit for feeding saline solution to the saline solution feeding passage of the rasp; and a suction unit for sucking the cut bone fragments from the rasp via the bone fragment exhausting passage and then exhausting the cut bone fragments to the outside.

The rasp may include a connector formed on one end of the rod having a cylindrical shape and connected to an adaptor of the powered surgical handpiece; and a cutter, formed on the other end of the rod, having a cutting blade formed at a lower portion of the cutter, a cavity formed in the cutter, and a plurality of grooves connecting the cavity to the cutting blade, wherein the saline solution feeding passage and the bone fragment exhausting passage formed in the cutter are extended to the outside of the cutter.

The powered surgical handpiece may include a main body; a motor installed in the main body; a mechanism for converting rotary motion of the motor into linear reciprocating motion; and an adaptor connecting the mechanism to the rasp. By the conversion of rotary motion of the motor into linear reciprocating motion, the adaptor moves forward and backward so that the linear reciprocating motion is supplied to the rasp connected to the adaptor, thereby allowing the rasp to cut bone. The powered surgical handpiece may have various structures.

Preferably, the above components of the powered surgical handpiece except for the mechanism may be variously modified according to the purpose of use.

The saline solution feeding unit serving to continuously or intermittently feed a constant amount of saline solution may have various structures. The suction unit serving to exhaust the cut bone fragments to the outside via suction may be connected to the bone fragment exhausting passage by a connection tube. Preferably, a bone fragment collector may be formed in the connection tube of the suction unit, thus allowing the device to collect bone fragments for use in implantation or culture as well as to contour facial bone.

When the powered surgical handpiece supplies linear reciprocating motion to the rasp connected to the adaptor of the handpiece, a cutting blade of the cutter grinds bone contacting the cutter. Then, the obtained bone fragments together with the fed saline solution are exhausted to the outside via the bone fragment exhausting passage. Accordingly, it is possible to continuously grind a desired site of facial bone.

The grooves formed in the cutter of the rasp serve to suck the bone fragments just after the cutting. The cavity is formed in the cutter, and connected to the saline solution feeding passage and the bone fragment exhausting passage. Alternatively, the cutter may be not hollowed, but include a throughhole connecting the inside of the cutter to the outside. In this case, a protector surrounding the outer surface of the cutter is formed such that there is a space between the cutter and the protector. The bone fragment exhausting passage and the saline solution feeding passage are connected to the space.

The fed saline solution serves to remove heat generated in bone-cutting so that the cutting can be continuously performed, and to prevent the aggregation of the bone fragments due to frictional heat so that the bone fragments are thoroughly exhausted to the outside.

BRIEF DESCRIPTION OF THE DRAWINGS

The above and other objects, features and other advantages of the present invention will be more clearly understood from the following detailed description taken in conjunction with the accompanying drawings, in which.

BEST MODE FOR CARRYING OUT THE INVENTION

Now, preferred embodiments of the present invention will be described in detail with reference to the annexed drawings.

Figure 1:
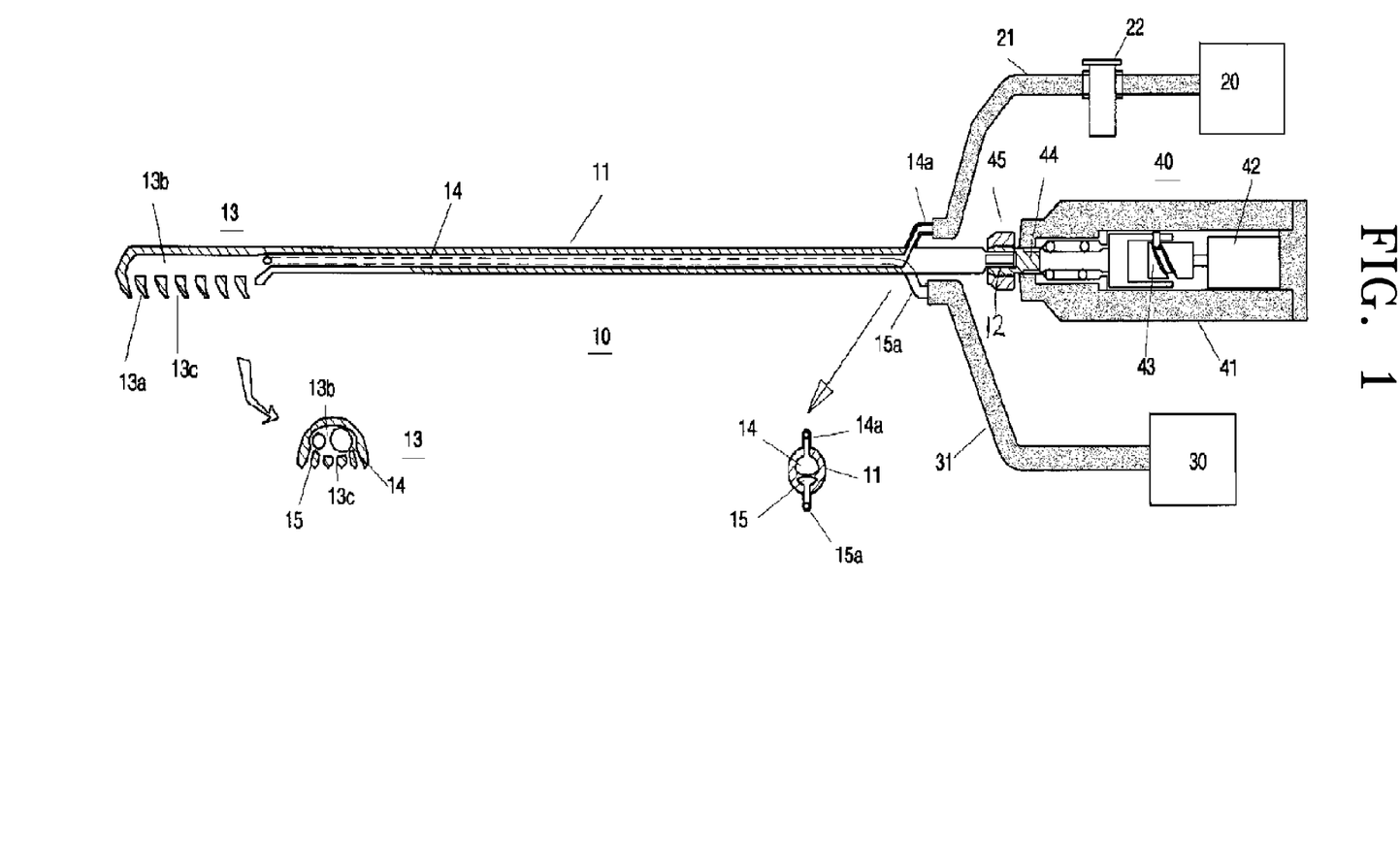
FIG. 1 is a schematic view of a facial bone contouring device using a hollowed rasp provided with non-plugging hole passing through a cutting plane in accordance with the present invention.

FIG. 1 is a schematic view of a facial bone contouring device in accordance with the present invention. A rasp 10 includes a rod 11, an adaptor connector 12 formed on an end of the rod 11, a cutter 13 formed on the other end of the rod 11, a bone fragment exhausting passage 14, and a saline solution feeding passage 15. The cutter 13 has a cutting blade 13a formed on the lower surface of the cutter 13, a cavity 13b formed in the cutter 13, and a plurality of grooves 13c passing through the cutting blade 13a so as to connect the cutting blade 13a to the cavity 13b. Two independent tubes are formed in the rod 11 and connected to the cavity 13b of the cutter 13, thus serving as the bone fragment exhausting passage 14 and the saline solution feeding passage 15.

Terminals of the two tubes formed in the rod 11 are connected to the cavity 13b formed in the cutter 13, and the other terminals of the two tubes formed in the cutter 13 are connected to external connection jacks 14a and 15a at a designated portion of the rod 11. The external connection jack 14a is connected to a connection tube 21 of a suction unit 20, and the external connection jack 15a is connected to a connection tube 31 of the saline solution feeding unit 30, thus feeding saline solution to the cutter 13 and exhausting cut bone fragments together with the saline solution to the outside.

Here, the rod 11 has a length of 100 to 120 mm, and an outer diameter of 3 to 5 mm. The cutter 13 has a length of 20 to 40 mm, and the cutting blade 13a has a width of approximately 2 mm. Each of the grooves 13c connecting the cavity 13b and the cutting blade 13a has a width of 0.8 to 1 mm, and the grooves 13c are spaced apart from each other by a distance of 0.8 to 1 mm.

In order to allow the bone fragments in a solid state to pass through the rod 11 more easily than the saline solution in a fluid state, the bone fragment exhausting passage 14 has a diameter 2 to 3 times as large as that of the saline solution feeding passage 15. Accordingly, it is possible to efficiently use a narrow hollow formed through the rod 11.

A powered surgical handpiece 40 includes a main body 41, a motor 42 installed in the main body 41 for supplying power, a mechanism 43 connected to a motor shaft for converting rotary motion of the motor 42 into linear reciprocating motion, and an adaptor 45 connected to a linear reciprocating shaft 44 connected to the mechanism 43. The handpiece 40 is assembled by inserting the adaptor connector 12 of the rasp 10 to the adaptor 45 and connecting the connection tubes 21 and 31 of the suction unit 20 and the saline solution feeding unit 30 to the external connection jacks 14a and 15a of the bone fragment exhausting and saline solution feeding passages 14 and 15.

The above embodiment of the facial bone contouring device allows an incision to be minimized, the cutter to be inserted beneath the skin via the incision, and the cutter to be delivered to a cutting site so that the cutting of bone and the exhausting of cut bone fragments are simultaneously performed. The saline solution fed into the incision via the saline solution feeding passage is sprayed into the cavity 13b of the cutter 13 under a proper pressure, so that a part of the sprayed saline solution is sprayed on a cutting plane and then sucked back together with the cut bone fragments via the bone fragment exhausting passage 14, and the other part of the sprayed saline solution is directly sucked back via the bone fragment exhausting passage 14 so as to increase suction efficiency.

In collecting bone for bone implantation, a bone fragment collector 22 is installed in the connection tube 21 of the suction unit 20. The bone fragment collector 22 serves to collect the cut bone fragments in undamaged state.

Figure 2:
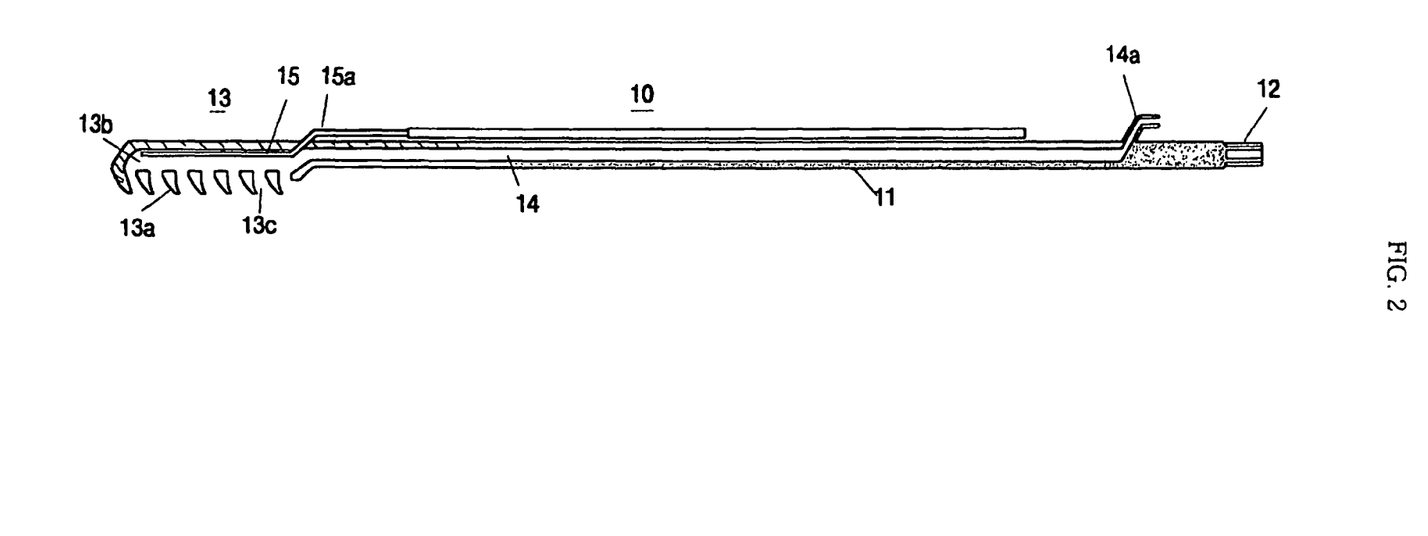
FIG. 2 is a schematic view of a further embodiment of a rasp of the present invention.

FIG. 2 illustrates a further embodiment of a rasp of the facial bone contouring device of the present invention. Here, a single tube is formed in the rod 11, and serves as the bone fragment exhausting passage 14. An external tube is installed on the outer surface of the rod 11, and serves as the saline solution feeding passage 15. A through-hole is formed through the cutter 13, and the saline solution feeding passage 15 is inserted into the cutter 13 via the through-hole and connected to the external connection jack 15a. The bone fragment exhausting and saline solution feeding passages 14 and 15 are correspondingly connected to the connection tubes.

This embodiment of the rasp has advantages in that it increases bone fragment exhausting capacity and saline solution feeding capacity at the same size.

Figure 3:
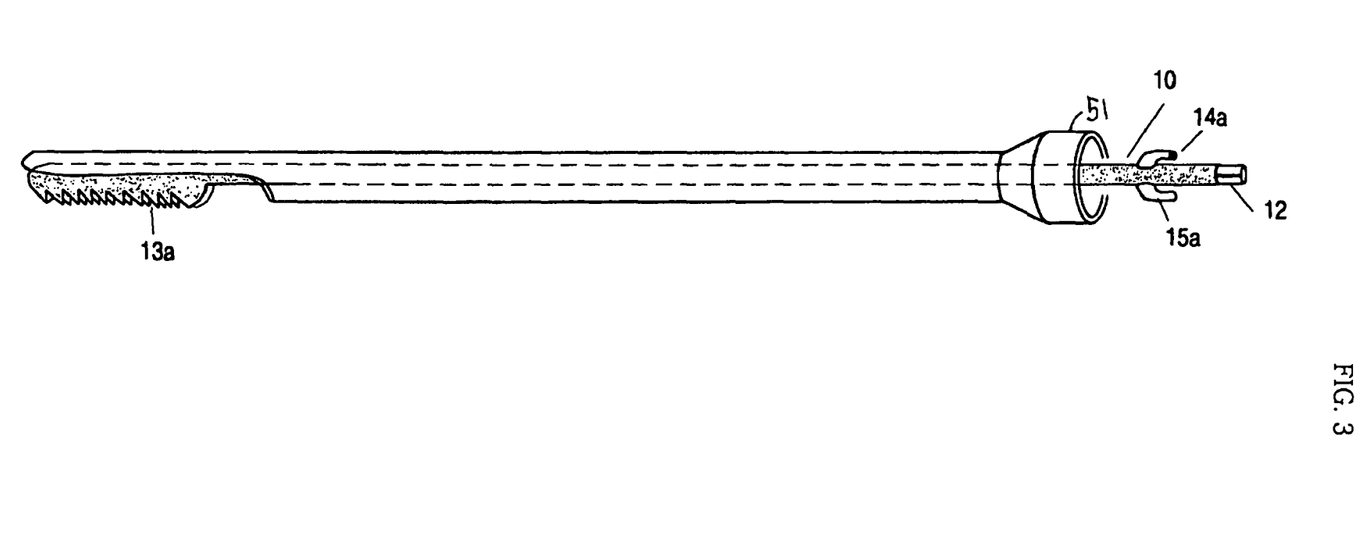
FIG. 3 is an assembled view of another embodiment of a rasp provided with a protector.

FIG. 3 illustrates another embodiment of a rasp provided with a protector 50 surrounding the outer surface of the rasp. The protector 50 is a cylindrical tube surrounding the rasp 10. The protector 50 includes a connector 51 formed at a terminal of the protector 50 and enlarged so as to be connected to the main body 41 of the handpiece 40, and an exposing portion 52 formed at the other terminal of the protector 50 for exposing the cutting blade 13a of the cutter 13.

Figure 4:
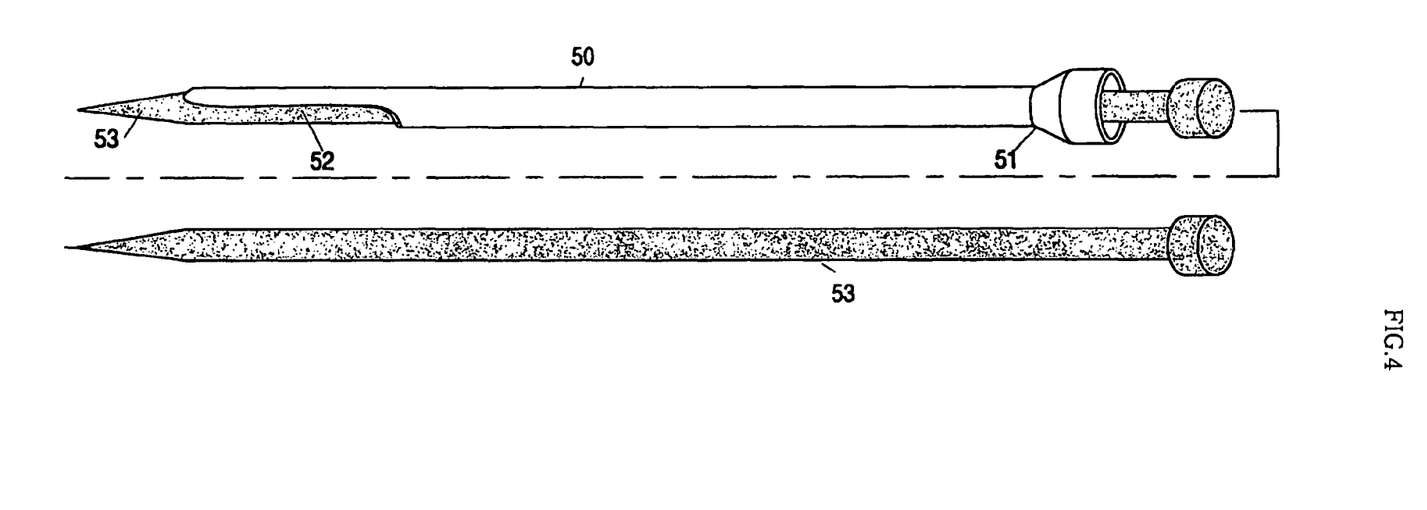
FIG. 4 is an exploded view of the rasp provided with a protector.

Under the state that the rasp 10 is inserted beneath the skin and is place against to a bone cutting site, the protector 50 surrounds the outer surface of the cutter 13 so that a space for moving the cutter 13 is obtained, thus preventing the cutter 13 from damaging peripheral soft tissues around the bone cutting site. As shown in FIG. 4, the protector 50 is separated from the rasp 10, and then inserted beneath the skin using a trocar 53 (a skin excavator with a sharpened tip) attached to a tip of the protector 50 so that the protector 50 is delivered to the bone cutting site. Then, the trocar 53 is eliminated from the protector 50, and the rasp 10 connected to the handpiece 40 is inserted into the protector 50. The protector 50 is fixed to the handpiece 40. Thereby, the rasp 10 can be placed at the bone cutting site via a minimum incision.

Figure 5:
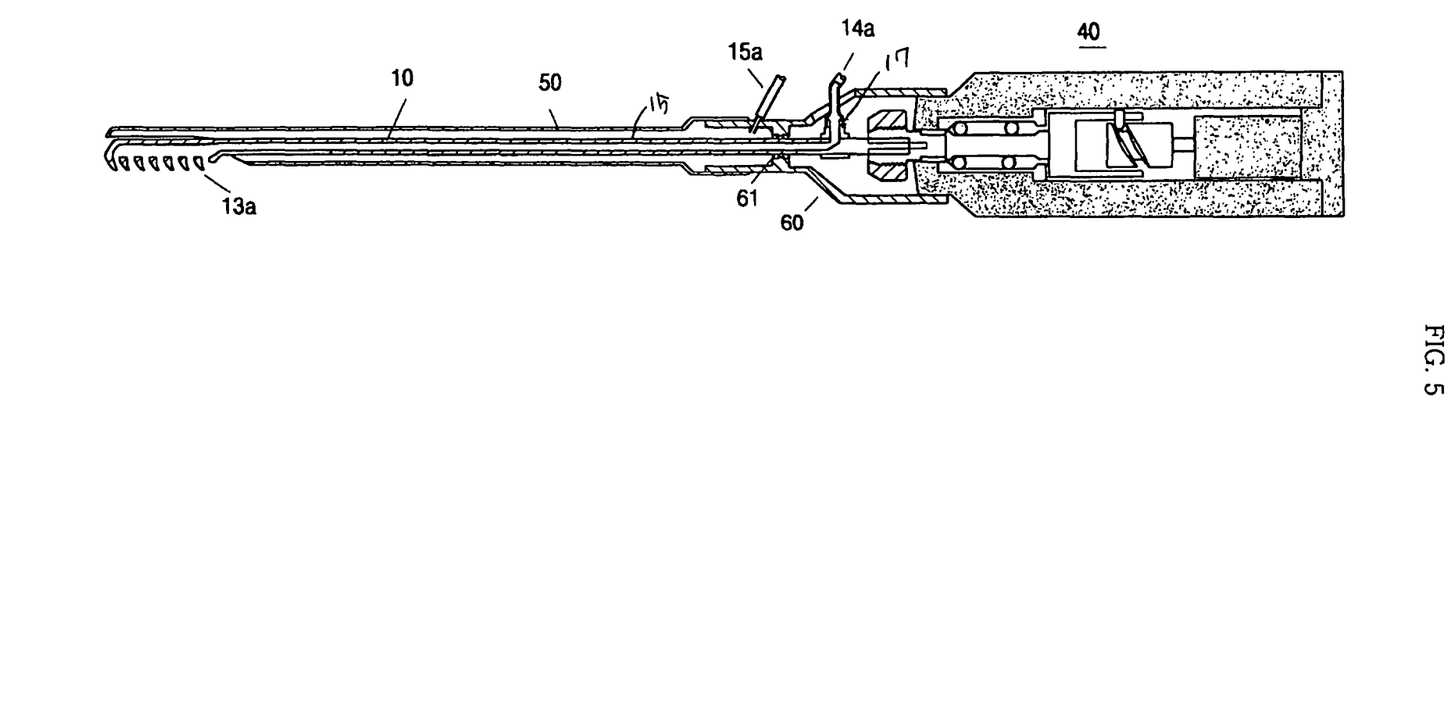
FIG. 5 is an assembled view of still another embodiment of a rasp provided with a protector.

FIG. 5 illustrates still another embodiment of a rasp provided with a protector. In this embodiment, the saline solution feeding passage 15 is formed between the protector 50 and the rod 11. Here, the rod 11 is connected to the handpiece 40 using an additional connection cap 60, and the rod 11 is connected to the inside of the connection cap 60 by a packing 61 so that water-tightness between the connection cap 60 and the rod 11 is maintained. The protector 50 is connected to an end of the connection cap 60, and the connection jack 5a connected to the saline solution feeding passage 15 is connected to a designated portion of the side surface of the connection cap 60, thereby connecting the rod 11 to the saline solution feeding unit. A connection ring 17 made of rubber is connected to a groove connected to the bone fragment exhausting passage 14 of the rod 11, and the connection jack 14a is connected to the end of the connection ring 17. The connection jack 14a is connected to the rod 11 via a long hole formed through the connection cap 60.

Figure 6:
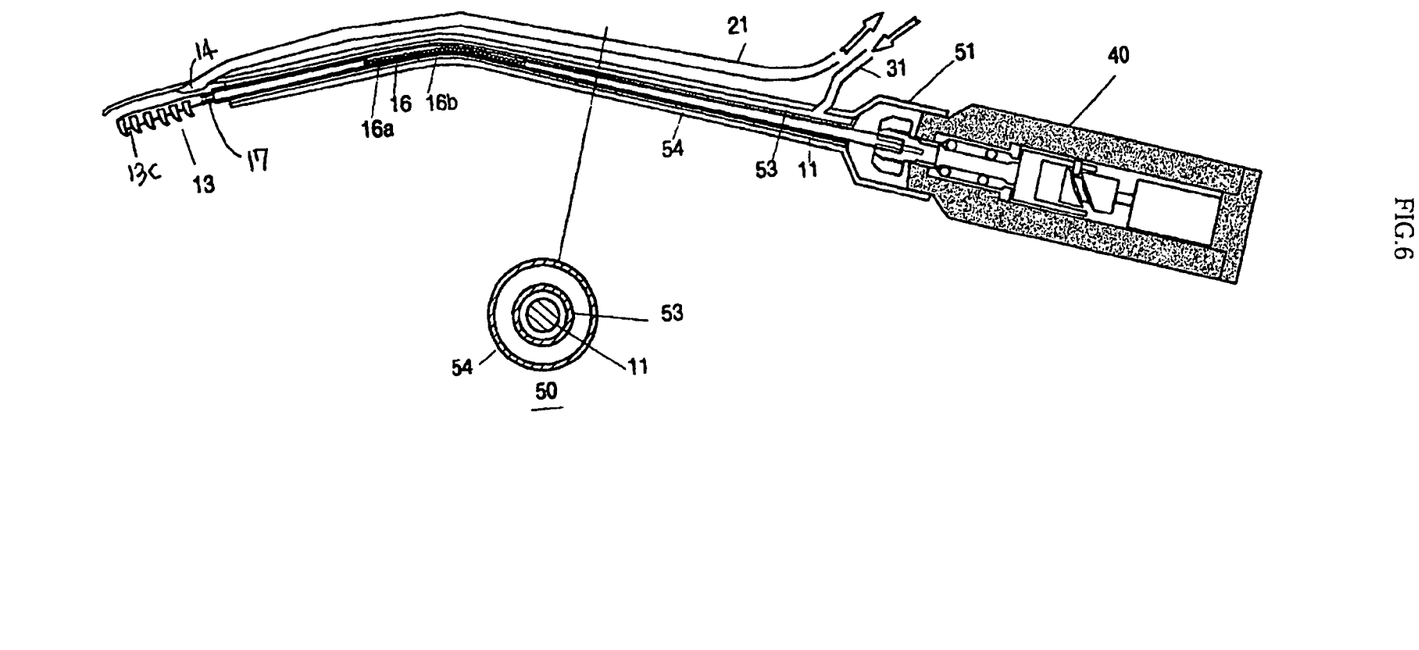
FIG. 6 is a schematic view of yet another embodiment of a rasp provided with a protector which is bendable at a designated portion.

FIG. 6 illustrates yet another embodiment of a rasp provided with a protector which is bendable at a designated portion. In this embodiment, the rod 11 provided with the protector 50 can be bent at a designated portion. Here, a bending portion 16 is formed at a predetermined portion of the rod 11, and the protector 50 is a double tube structure including an inner tube 53 and an outer tube 54. The saline solution feeding passage 15 is formed between the inner tube 53 and the outer tube 54 so that saline solution is fed to the cutter 13 via the saline solution feeding passage 15. The grooves 13c are vertically formed through the cutter 13. The bone fragment exhausting passage 14 is formed at the external surface of the tip of the protector 50 surrounding the cutter 13. The main body of the protector 50 is bent at a constant angle.

The protector 50 is directly connected to the handpiece 40 by the connector 51.

Preferably, a connector 17 is used to connect the rod 11 to the cutter 13, thus being detached from an interface between the rod 11 and the cutter 13 so that the components can be disinfected after assembling and disassembling of the rod 11 and the cutter 13.

This bending structure is very useful at a cutting site in which the approaching direction of the handpiece and the bone cutting direction are different. When the facial bone contouring device having the bending structure is operated under the condition that the rod and the protector are connected to the handpiece, the bending portion of the rod contacting the inner tube is bent and converts its travel direction, thus linearly moving the cutter in a different direction.

The bending portion 16 is formed by connecting chains or by running beads 16a through a wire 16b as shown in FIG. 6.

The protector 50 with a double tube structure feeds saline solution via a space between the inner tube 53 and the outer tube 54, and allows the inner tube 53 to maintain the linearity of the rod 11 including the bending portion 16. The tip of the protector 50 surrounding the cutter 13 serves to collect the cut bone fragments and then exhaust the cut bone fragments, and to provide a space for allowing the cutter 13 to move and then protect peripheral soft tissues around the bone cutting site from damage by the cutter 13.

Figure 7:
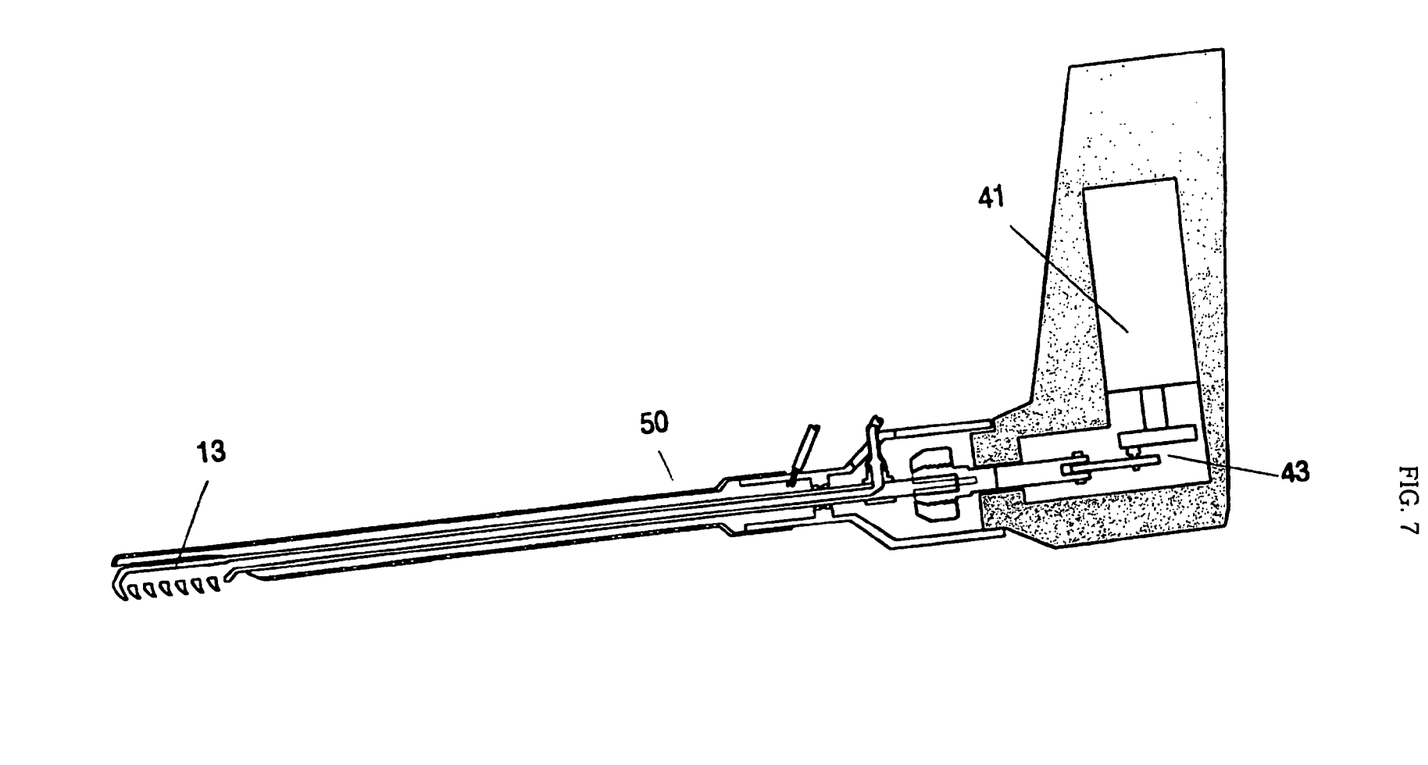
FIG. 7 is a schematic view of another embodiment of a handpiece.

FIG. 7 illustrates another embodiment of a handpiece. In this embodiment, the main body 41 of the powered surgical handpiece 40 is perpendicular to the linear moving direction of the rod. The mechanism 43 for converting rotary motion into linear reciprocating motion is assembled to have a crank shape. It is noted that the powered surgical handpiece of the facial bone contouring device of the present invention may have various structures.

Hereinafter, a surgical procedure for a mandibular angle reduction using the facial bone contouring device of the present invention will be described.

First, a stab incision is made at a designated site under the jaw or in oral cavity.

Second, after periosteotormy, a bone cutting site is selected, and then a guide serving as a raspatory is inserted into the selected cutting site.

Third, the protector is inserted into the bone cutting site along the guide.

Fourth, the guide is separated from the bone cutting site, and then the rasp attached to the handpiece is inserted into the bone cutting site along the protector.

Fifth, the facial bone contouring device is operated. Here, the rasp is occasionally pulled out of the bone cutting site so as to check whether the holes in the rasp are plugged or not.

The protector is maintained at the bone cutting site, but only the rasp is pulled out from the bone cutting site. Accordingly, it is possible to minimize the damage to skin.

INDUSTRIAL APPLICABILITY

As apparent from the above description, the facial bone contouring device of the present invention provides several improvements to facial bone contouring surgical procedure, as follows.

1. The facial bone contouring device of the present invention requires a small-sized incision, thus minimizing time required to secure operational visual field and suture, and allowing surgery to be accurately performed. Accordingly, it is possible to drastically shorten the time needed for the facial bone contouring surgery.

2. The facial bone contouring device of the present invention shortens the operation time and reduces the amount of damaged soft tissues, thus reducing swelling.

3. Compared with conventional saws, the facial bone contouring device of the present invention causes less damage to peripheral tissues, thus reducing the risk of medical accidents and promoting recovery after the operation.

4. Conventional rasps have a small collection rate of cut bone fragments, thus increasing the possibility of infection and the time taken to obtain a designated amount of the cut bone fragments required for use in implantation, and being unsuitable for use in implantation procedures. However, the facial bone contouring device of the present invention can collect a large quantity of the cut bone fragments for use as a material of an autogenous tissue for implantation. Further, the facial bone contouring device of the present invention can easily collect bone fragments from other bone as well as facial bone.

5. The facial bone contouring device of the present invention reduces the amount of scars generated by the operation.

6. The rasp of the facial bone contouring device of the present invention may be used independently. In this case, the rasp has improved efficiency, thus shortening the operation time.

7. Since the facial bone contouring device of the present invention simplifies the surgical process, it is possible to perform surgery under local anesthesia, as opposed to conventional general anesthesia, thus decreasing the risk of medical accidents due to anesthesia.

8. The facial bone contouring device of the present invention prevents the occurrence of a secondary angle after mandibulectomy for reducing the rectangular shape of the jaw, thus improving the results of cosmetic surgery. Further, the facial bone contouring device of the present invention cuts bone via several stages, thus increasing symmetry in surgery.

9. The facial bone contouring device of the present invention simply performs cleaning of the bone cutting site, thereby reducing the possibility of infection and simplifying the surgical process.

10. The facial bone contouring device of the present invention can be easily delivered to a bone cutting site via a small incision, thus being used in endoscopic operation for removing bone tumor or osteophyte. Further, surgeries, which were not conventionally performed by endoscopic techniques, can be performed by endoscopic techniques using the facial bone contouring device of the present invention.

11. The facial bone contouring device of the present invention is safer to use, thus providing a sense of safety to a patient.

12. The facial bone contouring device of the present invention comprises a passage for exhausting cut bone fragments, thus being continuously used to grind bone. In case that the rasp of the facial bone contouring device of the present invention has blades with a reduced width, the rasp can be used to cut bones the same as the conventional saws.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

The invention claimed is:

1. A facial bone contouring device, comprising:
a rasp including a rod, and a cutter, a saline solution feeding passage and a bone fragment exhausting passage formed in the cutter;
a powered surgical handpiece connected to the rasp for providing linear reciprocating motion to the rasp;
a saline solution feeding unit for feeding saline solution to the saline solution feeding passage of the rasp;
a suction unit for sucking the cut bone fragments from the rasp via the bone fragment exhausting passage and then exhausting the cut bone fragments to the outside; and
a protector, formed to have a cylindrical shape, configured to accept and surround the entire surface of the rod and a part of the cutter of the rasp, wherein the protector is configured to be inserted with a trocar,
wherein bone cutting is performed under the condition that the saline solution is fed into the rasp, and cut bone fragments are exhausted to the outside together with the saline solution, so that the bone cutting is continuously performed,
wherein the protector is configured to be separated from the rasp, to accept the trocar, to be delivered to a bone cutting site, to release the trocar, and to accept the rasp in the original place such that the rasp is disposed at the bone cutting site via a minimum incision,
wherein a plurality of non-plugging holes are formed through a cutting plane and between cutting blades formed at a lower portion of the cutter so as to exhaust cut bone fragments, wherein a cavity is formed in the cutter connected to the plurality of non-plugging holes, and wherein the cavity is connected to the bone fragment exhausting passage of the rasp.

2. The facial bone contouring device as set forth in claim 1, wherein a bone fragment collector is connected to the suction unit.

3. The facial bone contouring device as set forth in claim 1, wherein the rasp further includes a connector formed on one end of the rod having a cylindrical shape and connected to an adaptor of the powered surgical handpiece,
wherein the saline solution feeding passage and the bone fragment exhausting passage formed in the cutter are extended to the outside of the cutter.

4. The facial bone contouring device as set forth in claim 3, wherein the saline solution feeding passage and the bone fragment exhausting passage are formed in the rod.

5. The facial bone contouring device as set forth in claim 1, wherein the saline solution feeding passage is formed in the rod, and the bone fragment exhausting passage is formed by connecting the cavity in the cutter to an external connection jack protruding from the cutter.

6. The facial bone contouring device as set forth in claim 1, wherein a bending portion is formed at a designated portion of the rod, and wherein the protector has a double tube structure so that the saline solution feeding passage is formed between two tubes, and is bent at a designated angle.

* * * * *